US011850039B2

(12) United States Patent
Lindholm et al.

(10) Patent No.: US 11,850,039 B2
(45) Date of Patent: Dec. 26, 2023

(54) APPARATUS AND METHOD FOR DETERMINING A CHANGE IN LEFT VENTRICULAR TWIST OF A SUBJECT'S HEART

(71) Applicant: Nokia Technologies Oy, Espoo (FI)

(72) Inventors: Harri Lindholm, Helsinki (FI); Satu Rajala, Kagasala (FI)

(73) Assignee: Nokia Technologies Oy, Espoo (FI)

( * ) Notice: Subject to any disclaimer, the term of this patent is extended or adjusted under 35 U.S.C. 154(b) by 745 days.

(21) Appl. No.: 16/969,029

(22) PCT Filed: Feb. 8, 2019

(86) PCT No.: PCT/EP2019/053105
§ 371 (c)(1),
(2) Date: Aug. 11, 2020

(87) PCT Pub. No.: WO2019/166204
PCT Pub. Date: Sep. 6, 2019

(65) Prior Publication Data
US 2021/0030309 A1    Feb. 4, 2021

(30) Foreign Application Priority Data
Feb. 27, 2018  (EP) .................................... 18158949

(51) Int. Cl.
*A61B 5/02*    (2006.01)
*A61B 5/11*    (2006.01)
*A61B 5/0225*  (2006.01)

(52) U.S. Cl.
CPC ........ *A61B 5/1102* (2013.01); *A61B 5/02028* (2013.01); *A61B 5/0225* (2013.01); *A61B 2562/0219* (2013.01)

(58) Field of Classification Search
CPC ........ A61B 2562/0219; A61B 5/02028; A61B 5/02233; A61B 5/0225; A61B 5/1102
See application file for complete search history.

(56) References Cited

U.S. PATENT DOCUMENTS

2004/0260346 A1* 12/2004 Overall .............. A61B 5/02444
                                                 600/16
2007/0032749 A1   2/2007 Overall et al. ................ 600/595
2008/0071180 A1*  3/2008 Borgos ................. A61B 5/7239
                                                 600/490

(Continued)

OTHER PUBLICATIONS

Marcelli, Emanuela, et al., "First Experimental Evaluation of Cardiac Apex Rotation with an Epicardial Coriolis Force Sensor", American Society of Artificial Internal Organs Journal 2005, 6 pgs.

(Continued)

*Primary Examiner* — George Manuel
(74) *Attorney, Agent, or Firm* — Harrington & Smith (57) ABSTRACT

An apparatus and a method are described in which a signal is received from a gyroscope sensor mounted on a subject. The gyroscope sensor is configured to measure rotational movement of the subject's heart, the signal being indicative of a left ventricular twist of the subject's heart. A change in the left ventricular twist of the subject's heart caused by occlusion of blood flow by an arterial occlusion device configured to selectively occlude blood flow of the subject is determined.

15 Claims, 5 Drawing Sheets

(56) References Cited

U.S. PATENT DOCUMENTS

2011/0183990 A1* 7/2011 Antzelevitch ............. A61P 9/04
514/252.12

OTHER PUBLICATIONS

Tadi, Mojtaba Jafari, et al., "Gyrocardiography: A New Non-invasive Monitoring Method for the Assessment of Cardiac Mechanics and the Estimation of Hermodynamic Variables", Scientific Reports, published on-line Jul. 28 2017, 11 pgs.

* cited by examiner

APPARATUS AND METHOD FOR DETERMINING A CHANGE IN LEFT VENTRICULAR TWIST OF A SUBJECT'S HEART

CROSS REFERENCE TO RELATED APPLICATION

This patent application is a U.S. National Stage application of International Patent Application Number PCT/EP2019/053105 filed Feb. 8, 2019, which is hereby incorporated by reference in its entirety, and claims priority to EP 18158949.0 filed Feb. 27, 2018.

FIELD

The present specification relates to determining a change in left ventricular twist of a subject's heart.

BACKGROUND

A heart is a muscular organ that pumps blood through blood vessels. The human heart includes four chambers: namely a right atrium, a left atrium, a right ventricle and a left ventricle. The left atrium receives oxygenated blood from the lungs and the left ventricle pumps the oxygenated blood, via the aorta, around the body. Rotational movements, such as left ventricular twist (LV twist) are an important part of the pumping functionality of the heart. In particular, left ventricular twist is known to have a key role in the efficient ejection of blood from the heart. There is a need for method and apparatus for conducting effective left ventricular twist measurements.

SUMMARY

In a first aspect, this specification describes an a apparatus comprising: means for receiving a signal from a gyroscope sensor mounted on a subject, the gyroscope sensor configured to measure rotational movement of the subject's heart, the signal being indicative of a left ventricular twist of the subject's heart; and means for determining a change in the left ventricular twist of the subject's heart caused by occlusion of blood flow by an arterial occlusion device configured to selectively occlude the blood flow of the subject. The arterial occlusion device may be a blood pressure cuff. The gyroscope sensor may be mounted on a chest wall of the subject.

The apparatus may further comprise means for receiving a signal from a sensor configured to measure a function of the arterial occlusion device. The sensor configured to measure the function of the arterial occlusion device may measure a duration and/or an extent of the occlusion of the subject's blood flow.

The apparatus may further comprise means for providing an output signal configured to control a function of the arterial occlusion device. The output signal configured to control the function of the arterial occlusion device may be configured to control a duration and/or an extent of the occlusion of the subject's blood flow.

The apparatus may further comprise means (such as a neural network) for identifying patterns in changes in the signal indicative of the left ventricular twist of the subject's heart.

The said means of the apparatus may comprise: at least one processor and at least one memory including computer program code configured to, with the at least one processor, cause the performance of the apparatus.

In a second aspect, this specification describes a method comprising: receiving a signal from a gyroscope sensor mounted on a subject, the gyroscope sensor configured to measure rotational movement of the subject's heart, the signal being indicative of a left ventricular twist of the subject's heart; and determining a change in the left ventricular twist of the subject's heart caused by occlusion of blood flow by an arterial occlusion device configured to selectively occlude blood flow of the subject. The method may further comprise occluding the blood flow of the subject.

The method may further comprise determining an amount by which blood flow of the subject is occluded. The amount by which the blood flow of the user is occluded may be determined by measuring an extent and/or a duration of the occlusion of the subject's blood flow.

The method may further comprise controlling an amount by which the blood flow of the subject is occluded, for example by controlling a duration and/or an extent of the occlusion of the subject's blood flow.

The method may further comprise identifying patterns in changes in the signal indicative of the left ventricular twist of the subject's heart.

In a third aspect, this specification describes an apparatus configured to perform any method as described with reference to the second aspect.

In a fourth aspect, this specification describes computer-readable instructions which, when executed by computing apparatus, cause the computing apparatus to perform any method as described with reference to the second aspect.

In a fifth aspect, this specification describes a computer-readable medium having computer readable code stored thereon, the computer readable code, when executed by at least one processor, causes performance of: receiving a signal from a gyroscope sensor mounted on a subject, the gyroscope sensor configured to measure rotational movement of the subject's heart, the signal being indicative of a left ventricular twist of the subject's heart; and determining a change in the left ventricular twist of the subject's heart caused by occlusion of blood flow by an arterial occlusion device configured to selectively occlude blood flow of the subject.

In a sixth aspect, this specification describes a non-transitory computer-readable medium comprising program instructions stored thereon for performing at least the following: receiving a signal from a gyroscope sensor mounted on a subject, the gyroscope sensor configured to measure rotational movement of the subject's heart, the signal being indicative of a left ventricular twist of the subject's heart; and determining a change in the left ventricular twist of the subject's heart caused by occlusion of blood flow by an arterial occlusion device configured to selectively occlude blood flow of the subject.

In a seventh aspect, this specification describes an apparatus comprising: at least one processor; and at least one memory including computer program code which, when executed by the at least one processor, causes the apparatus to: receive a signal from a gyroscope sensor mounted on a subject, the gyroscope sensor configured to measure rotational movement of the subject's heart, the signal being indicative of a left ventricular twist of the subject's heart; and determine a change in the left ventricular twist of the subject's heart caused by occlusion of blood flow by an arterial occlusion device configured to selectively occlude blood flow of the subject.

BRIEF DESCRIPTION OF THE DRAWINGS

Example embodiments will now be described, by way of non-limiting examples, with reference to the following schematic drawings, in which.

DETAILED DESCRIPTION

Figure 1:
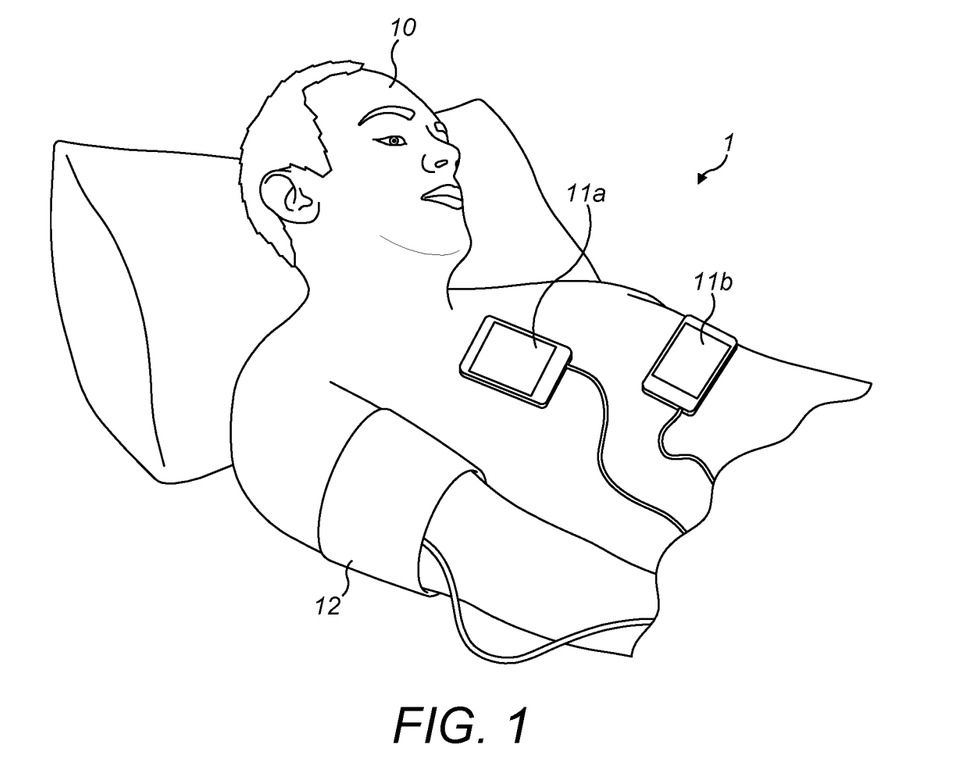
FIG. 1 shows a system in accordance with an example embodiment.

FIG. 1 shows a system, indicated generally by the reference numeral 1, in accordance with an example embodiment. The system 1 includes a first gyroscope sensor 11a and a second gyroscope sensor 11b mounted on a subject 10. The system 1 also includes an arterial occlusion device 12 for occluding blood flow in the subject 10, as discussed further below.

In some example embodiments the system 1 comprises only one gyroscope sensor. In other example embodiments there may be more than one gyroscope sensor. It should be noted that the positions of the gyroscope sensors 11a and 11b are provided by way of example only—alternative positions of the one or more gyroscope sensors are possible.

Gyrocardiography (GCG) is a recently developed methodology for measuring rotational movements of the heart. GCG provides a measurement of the mechanical work and multidirectional motions (rotational movements) of the heart muscle during a cardiac cycle. 3-axis GCG measures angular velocities with respect to three orthogonal axes, generally denoted as x, y and z. GCG can be measured with one or more gyroscope sensors mounted on the chest wall.

Contraction of the left ventricle of the heart is achieved by myocyte shortening of the oblique and circumferential fibres and following from a complex rearrangement of the microstructure of the left ventricle. This contraction causes a twisting motion around the long axis of the left ventricle and circumference shortening. The rotational movements of the heart, especially the left ventricular twist, play an important role in the efficient ejection of blood. Thus, the gyroscope sensor(s) (such as the first gyroscope sensor 11a and/or the second gyroscope sensor 11b) of the system 1 may be used to measure rotational movement of the heart of the subject 10, thereby obtaining one or more signals indicative of a left ventricular twist (LV twist) of the subject's heart.

Figure 2:
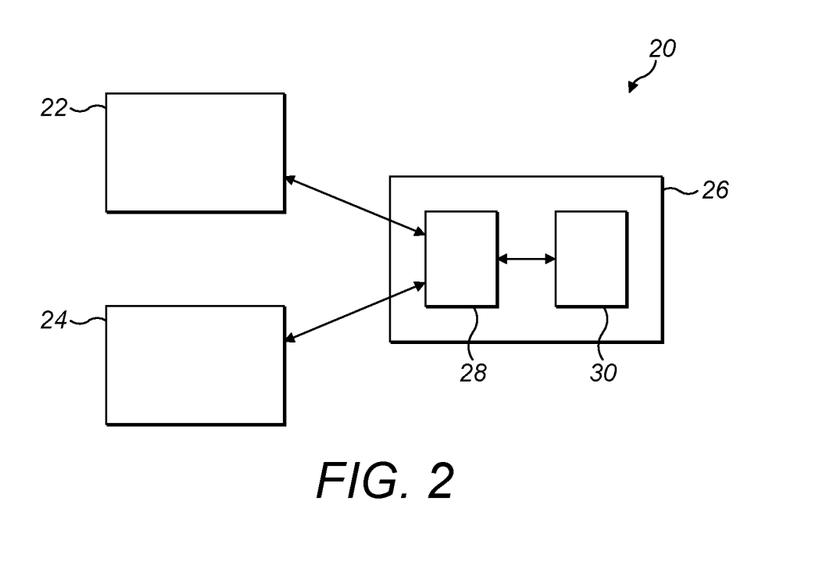
FIG. 2 is a schematic block diagram of a system in accordance with an example embodiment.

FIG. 2 is a schematic block diagram of a system, indicated generally by the reference numeral 20, in accordance with an example embodiment. The system 20 comprises one or more gyroscope sensors 22 (such as the first gyroscope sensor 11a and/or the second gyroscope sensor 11b described above), an arterial occlusion device 24 (such as the arterial occlusion device 12 described above) and a control module 26. The control module 26 includes a processor 28 and a memory 30. The memory 30 may include computer program code which may be executed by the processor 28.

Mobile phones and similar mobile communication devices may include a vibrating structure microelectromechanical system (MEMS) gyroscope sensor. Thus, the gyroscope sensor(s) 22 may be implemented using a MEMS gyroscope of a mobile phone or similar device. However, this is not essential to all embodiments. Any other suitable gyroscope sensor could be used. The gyroscope sensor may be placed on the chest of the subject (as shown in FIG. 1). Alternatively, the gyroscope sensor may be attached to the chest wall (e.g. using a strap or tape).

The arterial occlusion device 24 may be implemented using a blood pressure cuff. A blood pressure cuff may be inflatable in order to occlude blood flow in an artery below the cuff. A measuring unit associated with the blood pressure cuff can be used to provide a blood pressure measurement that may be an output of the arterial occlusion device 24.

As described further below, the arterial occlusion device 24 of the system 20 can be used to selectively occlude the blood flow of the subject 10. In this way, the arterial occlusion device 24 can be used as a physical provocation to the subject. The gyroscope sensor(s) 22 can then be used to measure rotational movement of the subject's heart (indicative of a left ventricular twist of the subject's heart) such that the processor 28 can determine a change in the left ventricular twist of the subject's heart caused by occlusion of blood flow by the arterial occlusion device 24 (i.e. in response to a physical provocation).

Figure 3:
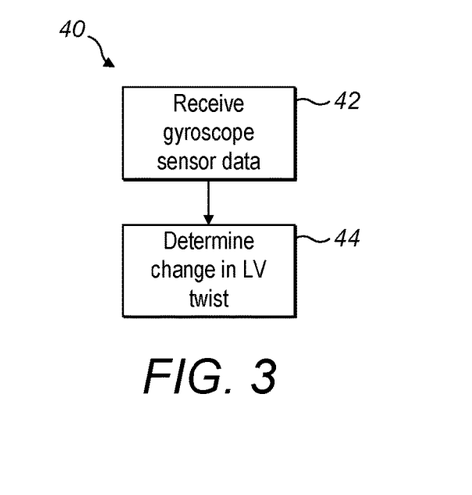
FIG. 3 is a flow chart showing an algorithm in accordance with an example embodiment.

FIG. 3 is a flow chart showing an algorithm, indicated generally by the reference numeral 40, in accordance with an example embodiment. The algorithm 40 starts at operation 42 where gyroscope sensor data is received from one or more gyroscope sensors (such as the gyroscope sensor 22 of the system 20). As described above, the gyroscope sensor data received in operation 42 is indicative of the left ventricle twist (LV twist) of a subject.

At operation 44, changes in the LV twist of the subject are identified. Possible implementations of operation 44 are described further below.

Figure 4:
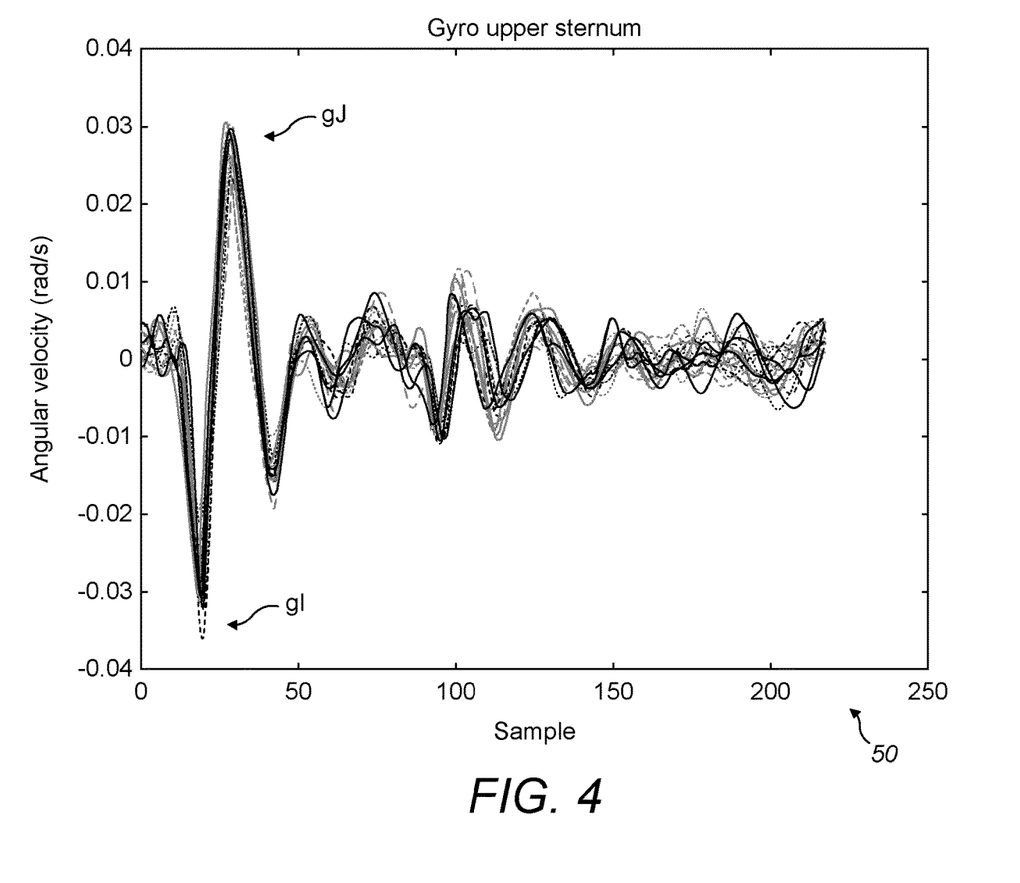
FIG. 4 is a plot showing an example of gyroscope sensor output data.

FIG. 4 is a plot showing an example of gyroscope sensor output signal, indicated generally by the reference numeral 50, measured from upper sternum of a subject. FIG. 4 shows data from several heartbeats in the same figure. The changes in the left ventricular twist (operation 44 of the algorithm 40 described above) can be evaluated from the gyrocardiography (GCG) signal shown in FIG. 4 by monitoring the amplitude of the signal and also the temporal parameters of the signal.

The temporal parameters of the signal 50 may include the time delays between the fiducial points of GCG signal of a single gyroscope sensor axis (e.g. y axis) or between fiducial points of GCG signals of multiple gyroscope sensor axes (e.g. x and y axis). For instance, GCG waveform annotation suggested by Jafari Tadi et al. [Jafari Tadi et al., Gyrocardiography: A New Non-invasive Monitoring Method for the Assessment of Cardiac Mechanics and the Estimation of Hemodynamic Variables, Scientific Reports, Volume 7, Article number: 6823, 2017] may be used to define the fiducial points (such as gI and gJ) of the GCG signal. Also, if an electrocardiogram (ECG) signal, i.e. the signal representing the electrical activation of the heart, is measured, the systolic and diastolic time intervals such as pre-ejection period (PEP) and left ventricular ejection time (LVET) may be obtained.

The temporal parameters may include the time delay gI-gJ, and Q-gI and Q-gJ (if ECG data is available).

An amplitude change between gI and gJ may also be determined. The amplitude between gI and gJ may be used as a cardiovascular parameter reflecting the strength of the heartbeat and it may correlate with other cardiovascular parameters such as ejection fraction. This enables monitoring of cardiac performance both during lifestyle related health promotion and remote monitoring in the medical domain.

Figure 5:
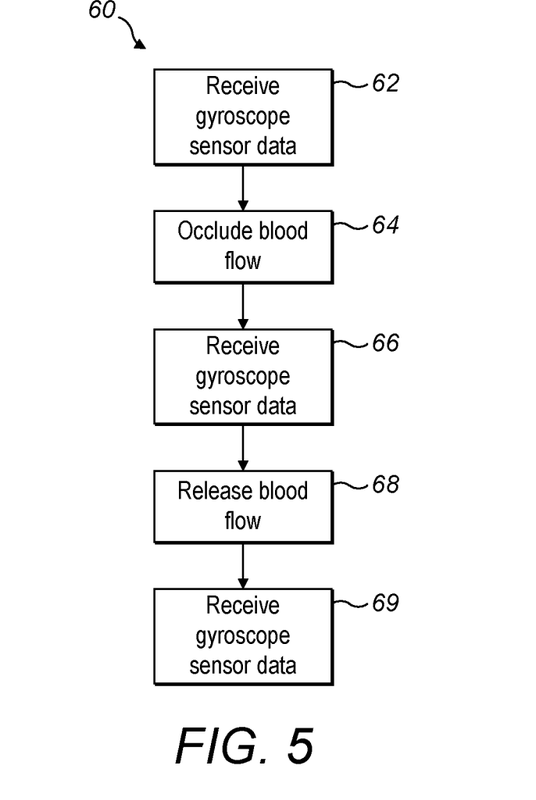
FIG. 5 is a flow chart showing an algorithm in accordance with an example embodiment.

FIG. 5 is a flow chart showing an algorithm, indicated generally by the reference numeral 60, in accordance with an example embodiment.

The algorithm 60 starts at operation 62, gyroscope sensor data is obtained, for example from the gyroscope sensor 22 discussed above.

At operation 64, an arterial occlusion device is used to occlude blood flow of the subject (such as the subject 10). At operation 66, gyroscope sensor data is obtained (with the blood flow occluded).

At operation 68, the arterial occlusion device is released such that the blood flow of the subject (such as the subject 10) is no longer occluded. At operation 69, gyroscope sensor data is obtained (with the blood flow no longer occluded).

The algorithm 60 therefore enables gyroscope sensor data to be obtained before, during and after occlusion of the blood flow. Since the gyroscope sensor data is indicative of LV twist, it is possible to determine a change in the left ventricular twist of the subject's heart caused by occlusion of blood flow by an arterial occlusion device configured to selectively occlude blood flow of the subject.

The system 20 may be used to implement the algorithm 60 described above.

The arterial occlusion device 24 may be used to implement the operations 64 and 68 of the algorithm 60. By way of example, the arterial occlusion device 24 may receive instructions from the processor 28, instructing the arterial occlusion device to occlude blood flow (operation 64) or to release blood flow (operation 68). The instructions from the processor 28 to the arterial occlusion device 24 may include an indication of the amount to which the blood flow should be occluded (such as the duration and/or the extent (e.g. the force applied) of the occlusion of the subject's blood flow). Alternatively, or in addition, the arterial occlusion device 24 may include a sensor to measure a function of the arterial occlusion device (such as the duration and/or the extent (e.g. the force applied) of the occlusion of the subject's blood flow); that data may be sent to the processor 28. Thus, as shown in FIG. 2, the communication between the processor 28 and the arterial occlusion device 24 may be bi-directional.

The gyroscope sensor 22 may be used to implement the operations 62, 66 and 69 of the algorithm 60. By way of example, the gyroscope sensor 22 may be used to obtain gyroscope sensor data (indicated of LV twist data) and to provide that sensor data to the processor 28.

As described above, the algorithm 60 obtains gyroscope sensor data before, during and after occlusion of the blood flow. This is not essential to all embodiments. One or more of those measurements may be omitted.

As described above, the arterial occlusion device 24 may provide data to the processor 28 regarding the function of the arterial occlusion device (such as the duration and/or the extent of the occlusion of the subject's blood flow). This is not essential to all embodiments. For example, the function of the arterial occlusion device may be apparent in the data obtained from the gyroscope sensor 22.

Figure 6:
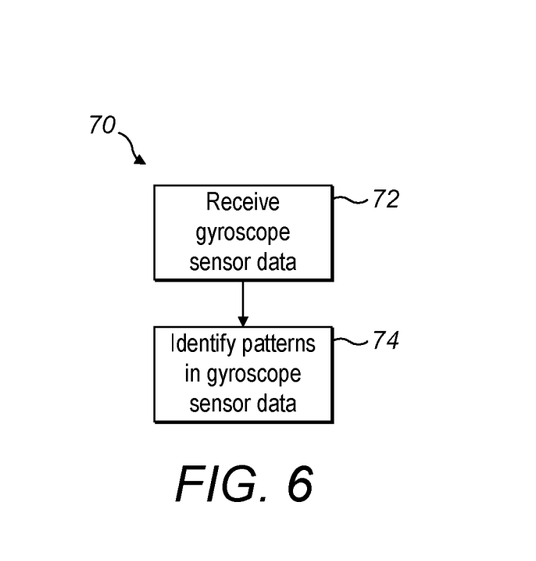
FIG. 6 is a flow chart showing an algorithm in accordance with an example embodiment.

FIG. 6 is a flow chart showing an algorithm, indicated generally by the reference numeral 70, in accordance with an example embodiment. At operation 72, gyroscope sensor data is received (for example from gyroscope sensor 22). As discussed above, the gyroscope data is indicated of LV twist.

The gyroscope sensor data may be collected over a period of time. At operation 74, patterns in the collected gyroscope data are identified. Such patters are therefore indicative of patterns in the associated LV twist data. The patterns identified in operation 74 may take many forms, including an increase in rotation, a reduction in rotation, an increase or reduction in the variation. The increase or reduction in rotation may be defined, for example, as the change in amplitude or in temporal parameters of a GCG signal, as described above.

Figure 7:
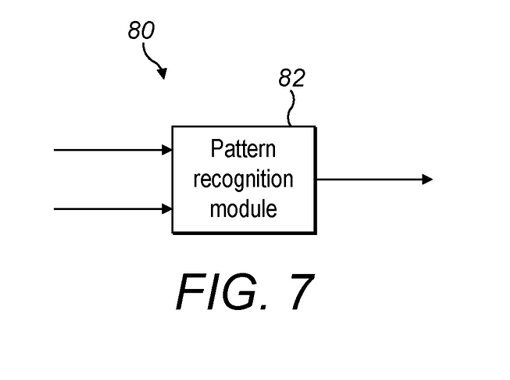
FIG. 7 is a block diagram of a system in accordance with an example embodiment.

FIG. 7 is a block diagram of a system, indicated generally by the reference numeral 80, in accordance with an example embodiment. The system 80 comprises a pattern recognition module 82 having a first input, a second input and an output. The first input receives gyroscope sensor data (for example data from the gyroscope sensor 22). The second input receives arterial occlusion device data (for example from the arterial occlusion device 24). The pattern recognition module 82 is configured to determine patterns in the data received at the first and second inputs and to provide such pattern information at the output. As discussed above, the second input (providing arterial occlusion device data) may be omitted in some embodiments, since that information may be incorporated within the gyroscope data received at the first input. The pattern recognition module 82 may, for example, be a neural network, however alternative arrangements are possible.

The pattern recognition module 82 may be implemented as part of the processor 28 described above. Alternative arrangements are possible. For example, a separate processor may be provided to implement the pattern recognition module. The pattern recognition or automatic annotation of fiducial points of a GCG signal may be based, for example, on machine learning approaches. Other alternative approaches include wavelet-based or Bayesian pattern recognition, support vector machines (SVM) and Hidden Markov Model (HMM) based methods.

In one embodiment, gyroscope sensor data can be obtained periodically over a long period of time, thereby enabling changes in the LV twist data to be monitored. By way of example, LV twist data may be collected each time a blood pressure measurement is taken (e.g. using the arterial occlusion device 24).

The frequency in which gyroscope sensor data might be obtained in accordance with the principles described herein may depend on a number of factors. For example, in the event that a person has been diagnosed with takotsubo cardiomyopathy (or stress-induced cardiomyopathy), data may be collected every day. For routine hypertension assessment, data may be collected once every six months.

The neural network (or other pattern recognition module) 82 of the system 60 may collect data over an extended period of time, thereby improving the ability of the neural network to identify patterns in the gyroscope sensor data outputs.

The examples described herein generally include a single gyroscope sensor. This is not essential to all embodiments. For example, multiple gyroscope sensors may be used to monitor rotational movement in different locations of the chest wall as the gyroscope signal may vary in these locations.

Figure 8:
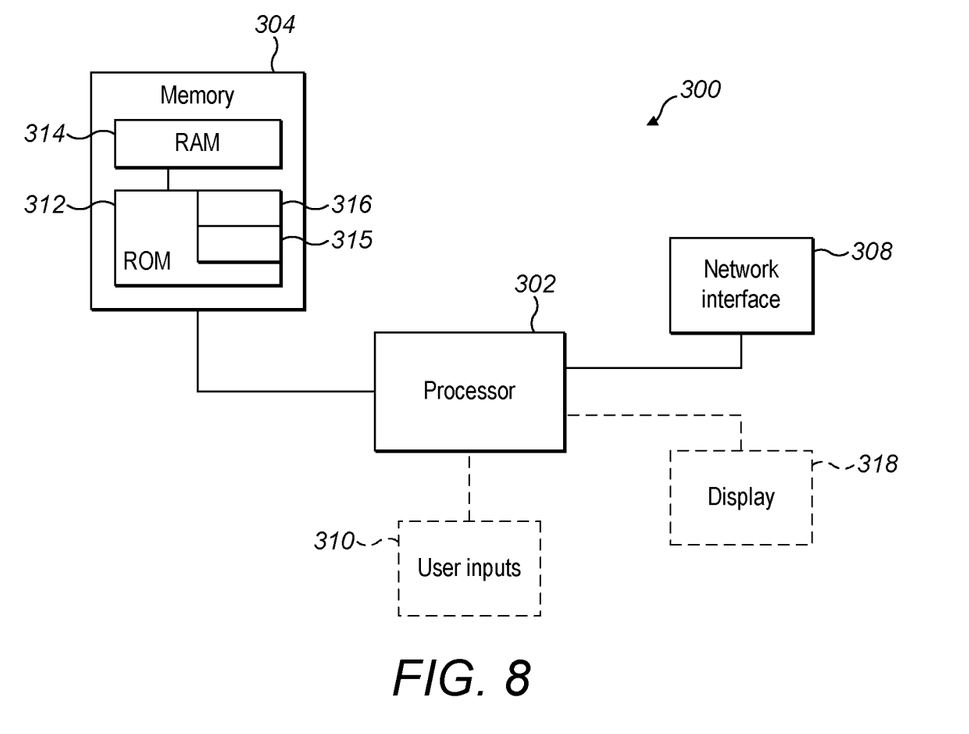
FIG. 8 is a block diagram of a system in accordance with an example embodiment.

For completeness, FIG. 8 is a schematic diagram of components of one or more of the modules described previously (e.g. the control module 26), which hereafter are referred to generically as processing systems 300. A processing system 300 may have a processor 302, a memory 304 coupled to the processor and comprised of a RAM 314 and ROM 312, and, optionally, user inputs 310 and a display 318. The processing system 300 may comprise one or more network interfaces 308 for connection to a network, e.g. a modem which may be wired or wireless.

The processor 302 is connected to each of the other components in order to control operation thereof.

The memory 304 may comprise a non-volatile memory, a hard disk drive (HDD) or a solid state drive (SSD). The ROM 312 of the memory 304 stores, amongst other things, an operating system 315 and may store software applications 316. The RAM 314 of the memory 304 is used by the processor 302 for the temporary storage of data. The operating system 315 may contain code which, when executed by the processor, implements aspects of the algorithms 40, 60 or 70.

The processor 302 may take any suitable form. For instance, it may be a microcontroller, plural microcontrollers, a processor, or plural processors.

The processing system 300 may be a standalone computer, a server, a console, or a network thereof.

In some embodiments, the processing system 300 may also be associated with external software applications. These may be applications stored on a remote server device and may run partly or exclusively on the remote server device. These applications may be termed cloud-hosted applications. The processing system 300 may be in communication with the remote server device in order to utilize the software application stored there.

Figure 9A:
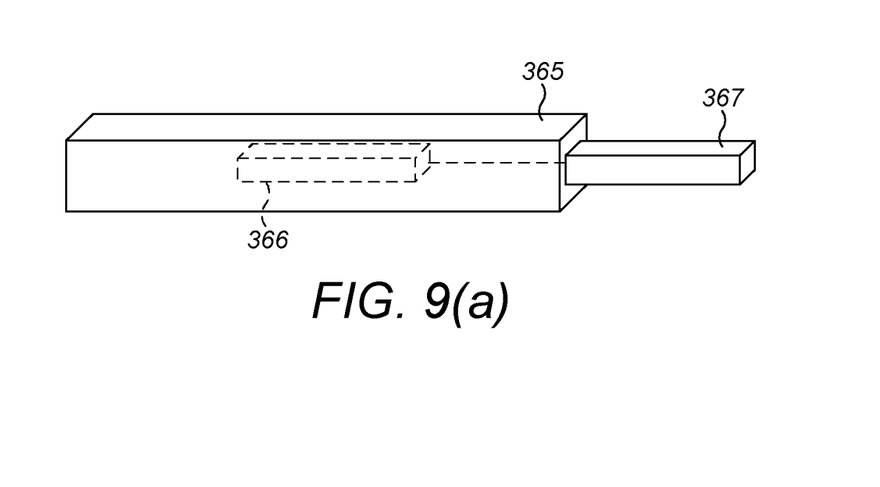
FIGS. 9a and 9b show tangible media, respectively a removable memory unit and a compact disc (CD) storing computer-readable code which when run by a computer perform operations according to embodiments.
Figure 9B:
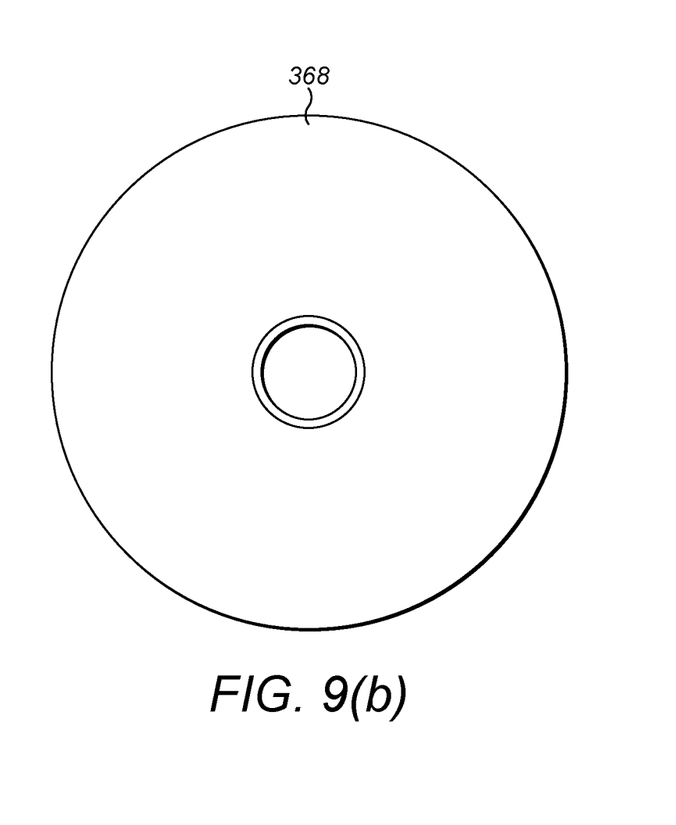

FIG. 9a and FIG. 9b show tangible media, respectively a removable memory unit 365 and a compact disc (CD) 368, storing computer-readable code which when run by a computer may perform methods according to embodiments described above. The removable memory unit 365 may be a memory stick, e.g. a USB memory stick, having internal memory 366 storing the computer-readable code. The memory 366 may be accessed by a computer system via a connector 367. The CD 368 may be a CD-ROM or a DVD or similar. Other forms of tangible storage media may be used.

Embodiments of the present invention may be implemented in software, hardware, application logic or a combination of software, hardware and application logic. The software, application logic and/or hardware may reside on memory, or any computer media. In an example embodiment, the application logic, software or an instruction set is maintained on any one of various conventional computer-readable media. In the context of this document, a "memory" or "computer-readable medium" may be any non-transitory media or means that can contain, store, communicate, propagate or transport the instructions for use by or in connection with an instruction execution system, apparatus, or device, such as a computer.

Reference to, where relevant, "computer-readable storage medium", "computer program product", "tangibly embodied computer program" etc., or a "processor" or "processing circuitry" etc. should be understood to encompass not only computers having differing architectures such as single/multi-processor architectures and sequencers/parallel architectures, but also specialised circuits such as field programmable gate arrays FPGA, application specify circuits ASIC, signal processing devices and other devices. References to computer program, instructions, code etc. should be understood to express software for a programmable processor firmware such as the programmable content of a hardware device as instructions for a processor or configured or configuration settings for a fixed function device, gate array, programmable logic device, etc.

As used in this application, the term "circuitry" refers to all of the following: (a) hardware-only circuit implementations (such as implementations in only analogue and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a server, to perform various functions) and (c) to circuits, such as a microprocessor(s) or a portion of a microprocessor(s), that require software or firmware for operation, even if the software or firmware is not physically present.

If desired, the different functions discussed herein may be performed in a different order and/or concurrently with each other. Furthermore, if desired, one or more of the above-described functions may be optional or may be combined. Similarly, it will also be appreciated that the flow diagrams of FIGS. 3, 5 and 6 are examples only and that various operations depicted therein may be omitted, reordered and/or combined.

It will be appreciated that the above described example embodiments are purely illustrative and are not limiting on the scope of the invention. Other variations and modifications will be apparent to persons skilled in the art upon reading the present specification.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims.

The invention claimed is:

1. An apparatus comprising:
   at least one processor; and
   at least one non-transitory memory storing instructions, that when executed by the at least one processor, cause the apparatus at least to:
   receive a signal from a gyroscope sensor mounted on a subject, the gyroscope sensor configured to measure rotational movement of the subject's heart, the signal being indicative of a left ventricular twist of the subject's heart;
   receive a signal from a sensor configured to measure a function of the arterial occlusion device, wherein the sensor configured to use bidirectional communication with the gyroscope sensor to measure the function of the arterial occlusion device comprising at least one of a duration or an extent of the occlusion of the subject's blood flow; and based on at least the bidirectional communication, determine a change in the left ventricular twist of the subject's heart caused by occlusion of blood flow by an arterial occlusion device configured to selectively occlude the blood flow of the subject.

2. An apparatus as claimed in claim 1, wherein the at least one non-transitory memory storing instructions is executed by the at least one processor too cause the apparatus at least to:

provide an output signal configured to control a function of the arterial occlusion device.

3. An apparatus as claimed in claim 2, wherein the output signal configured to control the function of the arterial occlusion device is configured to control at least one of a duration or an extent of the occlusion of the subject's blood flow.

4. An apparatus as claimed in claim 1, wherein the arterial occlusion device is a blood pressure cuff.

5. An apparatus as claimed in claim 1, wherein the gyroscope sensor is mounted on a chest wall of the subject.

6. An apparatus as claimed in claim 5, wherein the gyroscope sensor is mounted on an outside surface of a chest wall of the subject.

7. An apparatus as claimed in claim 5, wherein the gyroscope sensor is attached to a chest wall of the subject using a strap or tape.

8. An apparatus as claimed in claim 1, wherein the at least one non-transitory memory storing instructions is executed by the at least one processor too cause the apparatus at least to:

identify patterns in changes in the signal indicative of the left ventricular twist of the subject's heart.

9. A method comprising:

receiving a signal from a gyroscope sensor mounted on a subject, the gyroscope sensor configured to measure rotational movement of the subject's heart, the signal being indicative of a left ventricular twist of the subject's heart;

receiving a signal from a sensor configured to measure a function of the arterial occlusion device, wherein the sensor configured to use bidirectional communication with the gyroscope sensor to measure the function of the arterial occlusion device comprising at least one of a duration or an extent of the occlusion of the subject's blood flow; and based on at least the bidirectional communication, determining a change in the left ventricular twist of the subject's heart caused by occlusion of blood flow by an arterial occlusion device configured to selectively occlude blood flow of the subject.

10. A method as claimed in claim 9, further comprising occluding the blood flow of the subject.

11. A method as claimed in claim 9, further comprising determining an amount by which blood flow of the subject is occluded.

12. A method as claimed in claim 11, wherein the amount by which the blood flow of the user is occluded is determined by measuring at least one of an extent or a duration of the occlusion of the subject's blood flow.

13. A method as claimed in claim 9, further comprising controlling an amount by which the blood flow of the subject is occluded.

14. A method as claimed in claim 9, further comprising identifying patterns in changes in the signal indicative of the left ventricular twist of the subject's heart.

15. A computer-readable medium having computer readable code stored thereon, the computer readable code, when executed by at least one processor, causes performance of:

receiving a signal from a gyroscope sensor mounted on a subject, the gyroscope sensor configured to measure rotational movement of the subject's heart, the signal being indicative of a left ventricular twist of the subject's heart;

receiving a signal from a sensor configured to measure a function of the arterial occlusion device, wherein the sensor configured to use bidirectional communication with the gyroscope sensor to measure the function of the arterial occlusion device comprising at least one of a duration or an extent of the occlusion of the subject's blood flow; and based on at least the bidirectional communication, determining a change in the left ventricular twist of the subject's heart caused by occlusion of blood flow by an arterial occlusion device configured to selectively occlude blood flow of the subject.

* * * * *